(12) United States Patent
Yang et al.

(10) Patent No.: US 12,193,663 B2
(45) Date of Patent: Jan. 14, 2025

(54) END EFFECTOR FOR STAPLER

(71) Applicants: EZISURG MEDICAL CO., LTD., Shanghai (CN); EZISURG (SUZHOU) MEDICAL CO., LTD., Jiangsu (CN); ZHEJIANG EASYSCOPY MEDICAL CO., LTD., Zhejiang (CN)

(72) Inventors: Jun Yang, Shanghai (CN); Chuangang Tang, Shanghai (CN); Menghui Liao, Shanghai (CN)

(73) Assignees: EZISURG MEDICAL CO., LTD., Shanghai (CN); EZISURG (SUZHOU) MEDICAL CO., LTD., Jiangsu (CN); ZHEJIANG EASYSCOPY MEDICAL CO., LTD., Zhejiang (CN)

( * ) Notice: Subject to any disclaimer, the term of this patent is extended or adjusted under 35 U.S.C. 154(b) by 130 days.

(21) Appl. No.: 18/027,819

(22) PCT Filed: Sep. 22, 2021

(86) PCT No.: PCT/CN2021/119526
§ 371 (c)(1),
(2) Date: Mar. 22, 2023

(87) PCT Pub. No.: WO2022/063104
PCT Pub. Date: Mar. 31, 2022

(65) Prior Publication Data
US 2023/0277174 A1 Sep. 7, 2023

(30) Foreign Application Priority Data
Sep. 22, 2020 (CN) .......................... 202011004778.1

(51) Int. Cl.
*A61B 17/072* (2006.01)

(52) U.S. Cl.
CPC .. *A61B 17/072* (2013.01); *A61B 2017/07271* (2013.01); *A61B 2017/07285* (2013.01)

(58) Field of Classification Search
CPC ............ A61B 17/072; A61B 17/07207; A61B 2017/07285; A61B 2090/034
(Continued)

(56) References Cited

U.S. PATENT DOCUMENTS 5,865,361 A * 2/1999 Milliman ............. A61B 17/068
227/176.1
9,681,870 B2 * 6/2017 Baxter, III ....... A61B 17/07207
(Continued)

FOREIGN PATENT DOCUMENTS

CN 111134752 A 5/2020
CN 111616763 A 9/2020
(Continued)

OTHER PUBLICATIONS

International Search Report issued in corresponding International Application PCT/CN2021/119526, and an English Translation, mailed Dec. 22, 2021.
(Continued)

*Primary Examiner* — Alentin Neacsu
(74) *Attorney, Agent, or Firm* — Burris Law, PLLC (57) ABSTRACT

Disclosed is an end effector for a stapler, including a knife holder, and a staple cartridge unit and a staple anvil which are pivotally connected to achieve relative opening and closing. The staple cartridge unit includes a staple cartridge base and a detachable staple cartridge assembly. The knife holder includes a knife holder body and a limiting projection. The limiting projection is arranged between the knife holder body and the knife holder body. When the staple cartridge assembly is detached or mounted relative to the staple cartridge base, the limiting projection of the knife
(Continued)

holder abuts against a proximal end portion of the staple cartridge base to stop the staple cartridge base. When the knife holder leaves the initial retraction position, the limiting projection of the knife holder is separated from the staple cartridge base.

16 Claims, 7 Drawing Sheets

(58) Field of Classification Search
USPC .................................................... 227/176.1
See application file for complete search history.

(56) References Cited

U.S. PATENT DOCUMENTS

| 10,499,917 | B2* | 12/2019 | Scheib | ................. | A61B 17/105 |
| 2009/0206137 | A1* | 8/2009 | Hall | ................. | A61B 17/07207 |
| | | | | | 227/176.1 |
| 2015/0173745 | A1* | 6/2015 | Baxter, III | ....... | A61B 17/07207 |
| | | | | | 227/176.1 |
| 2023/0277174 | A1* | 9/2023 | Yang | .................... | A61B 17/072 |
| | | | | | 227/176.1 |
| 2024/0318417 | A1* | 9/2024 | Larson | ................. | E03F 5/0408 |

FOREIGN PATENT DOCUMENTS

| CN | 214632231 U | 11/2021 |
| JP | 2005080702 A | 3/2005 |

OTHER PUBLICATIONS

Written Opinion issued in corresponding International Application PCT/CN2021/119526, mailed Dec. 22, 2021, and English Translation thereof.

* cited by examiner

END EFFECTOR FOR STAPLER

CROSS REFERENCE TO RELATED APPLICATION

This application is a national phase of International Application No. PCT/CN2021/119526, filed on Sep. 22, 2021, which claims priority to Chinese Patent Application No. 202011004778.1, filed on Sep. 22, 2020 in China National Intellectual Property Administration and entitled "END EFFECTOR FOR STAPLER". The disclosures of the above applications are incorporated herein by reference in their entirety.

FIELD

The present disclosure relates to the technical field of medical apparatus and instruments, in particular to an end effector for a stapler.

BACKGROUND

Generally speaking, a stapler can be widely used for tissue suture and cutting in surgery. The stapler can generally consist of an end effector located at a distal end, a handle portion located at a proximal end, and a connecting transmission portion connected between the end effector and the handle portion. The end effector refers to a part of the stapler that is used to contact and manipulate patients' tissues. The connecting transmission portion can be provided with a hollow tube. A drive rod which can slide back and forth along the axial direction of the hollow tube is arranged in the hollow tube to actuate the end effector. The drive rod can usually be connected to an actuator of the stapler handle at the proximal end portion. When an operation is performed, the mechanism on the handle slides the drive rod along the hollow tube, so that the end effector manipulates the tissue.

The end effector of the stapler can generally include a knife holder which can move between the proximal and distal ends, and a staple cartridge unit and a staple anvil which are pivotally connected to achieve relative opening and closing, wherein the staple cartridge unit includes a staple cartridge base and a staple cartridge assembly detachably mounted to the staple cartridge base. The staple cartridge assembly of most reusable stapler on the market is mostly disposable.

In an embodiment of the end effector, for example, as described in U.S. Pat. No. 5,865,361, the staple cartridge assembly is fixedly installed on the staple cartridge base, the actuator is detachably connected with the connecting transmission portion, after the actuator is used once, it can be disassembled from the connection transmission portion. In other embodiments of the end effector, such as described in Ethicon's patent CN101507644B, the actuator is fixedly connected with the connecting transmission portion, the staple cartridge assembly and the staple cartridge base are detachably connected, the staple cartridge assembly can be detached from the staple cartridge base after a single use, and the actuator can be used several times in the same operation after installing a new staple cartridge assembly.

However, in the second embodiment described above, disadvantageously, in the process of installation, the end effector's jaw opening function is achieved by an elastic sheet, which cannot fix the staple cartridge base, making it very difficult and inconvenient for the staple cartridge assembly to be disassembled from the staple cartridge base. And the disassembly needs to be done with tools, resulting in a large workload and reducing work efficiency when assembling and disassembling the staple cartridges.

Accordingly, there is a need in the art for an end effector for a stapler that eliminates or at least mitigates all or part of the defects in the prior art described above.

SUMMARY

In view of the above technical problems existing in the prior art, the present disclosure aims to provide an end effector for a stapler, which enables easy removal and/or installation of the staple cartridge assembly of the end effector relative to the staple cartridge base, thereby enabling easy and quick removal and/or installation of the staple cartridge unit. The present disclosure is particularly applicable to an endoscopic cutting stapler.

It is emphasized herein that, unless otherwise stated, terms used herein are consistent with the common meaning of various technical terms in the art, as defined in various technical dictionaries, textbooks, etc.

As used herein, orientation is generally expressed with reference to the instrument operator, with a location relatively close to the instrument operator being referred to as the "proximal end" and a location relatively distant from the instrument operator being referred to as the "distal end". Further, as used herein, the length direction of the stapler can be referred to as the axial direction.

To this end, according to some embodiments of the present disclosure, provided is an end effector for a stapler, the end effector includes a knife holder movable in an axial direction (between the proximal end and the distal end); and a staple cartridge unit and a staple anvil, pivotally connected to achieve relative opening and closing, wherein the staple cartridge unit includes a staple cartridge base and a staple cartridge assembly detachably mounted to the staple cartridge base;

wherein the knife holder comprises a knife holder body and at least one limiting projection disposed near a distal end portion of the knife holder body and extending perpendicularly outward from the knife holder body in a direction away from the knife holder body, wherein the limiting projection is arranged between at least one edge of the knife holder body close to the staple cartridge base and a center of the knife holder body; and when the staple cartridge assembly is detached from or mounted to the staple cartridge base, the staple cartridge unit is in an open position, the knife holder is in an initial retraction position, and the limiting projection of the knife holder abuts against a proximal end portion of the staple cartridge base to stop the staple cartridge base; and when the knife holder leaves the initial retraction position, the limiting projection of the knife holder is separated from the staple cartridge base.

Further, in some embodiments, the proximal end portion of the staple cartridge base is provided with a contact portion corresponding to the limiting projection, the limiting projection is provided with an abutment portion corresponding to the contact portion, and when the limiting projection of knife holder abuts against the contact portion of the staple cartridge base to stop the staple cartridge base, the abutment portion of limiting projection may contact and abut against the contact portion of the staple cartridge base.

Preferably, the abutment portion is a plane for face-to-face contact with the contact portion or a linear side edge for line-to-face contact with the contact portion.

Further, in some embodiments, the contact surface of the staple cartridge base is flat or substantially flat. Note that the term "substantially flat" may be used herein to denote a flat shape that is nearly flat despite some unevenness.

Further, in some embodiments, the limiting projection of the knife holder may be made of metal. Preferably, the limiting projection of the knife holder and the knife holder body are made of the same metallic material, for example steel.

Typically, the staple cartridge assembly can be disassembled or installed relative to the staple cartridge base by mechanical disassembly or mechanical installation when the limiting projection of the knife holder is against the contact portion of the staple cartridge base to stop the staple cartridge base.

Further, in some embodiments, the knife holder comprises a first wing plate disposed at the at least one edge for closing the staple cartridge unit and a space between the limiting projection and the first wing plate, when the staple cartridge unit pivots relative to the staple anvil between an open position and a closed position, the proximal end portion of the staple cartridge base reciprocates within the space.

Further, in some embodiments, the limiting projection may be integrally formed with the knife holder body.

In another alternative embodiment, the limiting projection may be fixedly connected to the knife holder body in the case where the limiting projection is formed separately with respect to the knife holder body.

Further, in some embodiments, a longitudinal section parallel to an axial direction of the limiting projection may be in a polygonal or circular shape.

Preferably, in some embodiments, the limiting projection may be a column having a convex hexagonal longitudinal section.

Preferably, in some embodiments, the limiting projection may be a square column.

Preferably, in some embodiments, the limiting projection may be a cylinder.

Further, in some embodiments, the limiting projection may be welded to the knife holder body.

In another alternative embodiment, the knife holder may be provided with a through hole penetrating through the knife holder body between the at least one edge and a center of the knife holder body. Preferably, the limiting projection is a pin inserted in an interference fit to the through hole of the knife holder, and the pin may extend from the through hole by a proper length.

Further, in some embodiments, the staple cartridge assembly may comprise a U-shaped staple cartridge and a cover plate arranged inside the staple cartridge and extending along a U-shaped circumferential direction of the staple cartridge, so that a cross-shaped guide channel may be arranged between the staple cartridge and the cover plate, when the knife holder leaves the initial retraction position and moves toward a distal end in an axial direction to drive the staple cartridge unit to pivot to the closed position, the limiting projection may disengage from the proximal end portion of the staple cartridge base to move the knife holder through the guide channel. Preferably, the cross-shape of the guide channel may be configured to comprise an intermediate body portion for allowing the knife holder body to move through, and a lateral gap perpendicular to the intermediate body portion and extending to two sides in a direction away from the intermediate body portion for allowing the limiting projection to move through.

Further, in some embodiments, the staple cartridge assembly further comprises a staple driver for pushing out a titanium staple, and a movable slider arranged in the intermediate body portion, the slider being initially arranged at a proximal end of the intermediate body portion, and when the knife holder moves toward a distal end in the axial direction, the knife holder body moves into the intermediate body portion, and at the same time the limiting projection moves into the lateral gap, and with the knife holder moving, the distal end portion of the knife holder body may push the slider to slide in the intermediate body portion, so that the slider is capable of pushing the staple driver in the intermediate body portion to push out the titanium staple.

Further, the end effector for the stapler according to any one of the above-described embodiments is applicable for an endoscopic cutting stapler.

The end effector for the stapler provided according to the embodiments of the present disclosure may present the following beneficial effects:

According to the present disclosure, by providing the limiting projection for fixing the staple cartridge base at the knife holder, when the knife holder is in the initial retraction position and the staple cartridge assembly is removed or installed relative to the staple cartridge base, the limiting projection can resist the staple cartridge base under an external force, thereby stopping the staple cartridge base and enabling the staple cartridge assembly of the end effector to be easily disassembled or mounted relative to the staple cartridge base, so that the installation, disassembly and replacement of the staple cartridge unit are convenient and quick.

Furthermore, the present disclosure can provide a contact portion of the staple cartridge base and an abutment portion of the limiting projection fitting the contact portion, which can increase the friction between the limiting projection and the staple cartridge base, so that the staple cartridge base can be more firmly pressed against the limiting projection.

Furthermore, according to the present disclosure, by providing the guide channel for allowing the knife holder to move through at the staple cartridge assembly, the knife holder including the limiting projection can move stably while moving in the staple cartridge assembly without interfering with the operation of other parts of the staple cartridge assembly. Further, the staple cartridge assembly may further include a movable slider disposed in the intermediate body portion of the guide channel such that as the knife holder moves in the staple cartridge assembly, the distal end portion of the knife holder body pushes the slider to slide in the intermediate body portion to enable the slider to easily push the staple driver in the staple cartridge assembly to push out the titanium staple.

The present disclosure is particularly applicable to an endoscopic cutting stapler.

The present disclosure features a simple structure and easy and convenient operation.

BRIEF DESCRIPTION OF THE DRAWINGS

The accompanying drawings, which are illustrated herein, serve to provide a further understanding for the present disclosure and form a part of the present disclosure, and the exemplary embodiments of the present disclosure as well as the illustrations thereof serve to explain the present disclosure and do not constitute an undue limitation of the present disclosure. In the drawings.

DETAILED DESCRIPTION

In order to make objectives, technical solutions, and advantages of the embodiments of the present disclosure clearer, the technical solutions in the embodiments of the present disclosure will be clearly and completely described with reference to the embodiments in combination with the accompanying drawings. Clearly, the described embodiments are not all embodiments but only part of embodiments of the present disclosure. Based on the embodiments of the present disclosure, all other embodiments obtained by those skilled in the art without creative work shall fall within the protection scope of the present disclosure.

First, as mentioned above, the stapler can generally consist of an end effector located at a distal end, a handle portion located at a proximal end, and a connecting transmission portion connected between the end effector and the handle portion. The connecting drive portion may be provided with a hollow tube, and a drive rod slidable back and forth in an axial direction may be provided within the hollow tube. The drive rod is usually connected to the actuator of the stapler handle portion at the proximal end portion, and to the end effector at the distal end portion. When an operation is performed, the actuator actuates the drive rod to move in the axial direction so as to actuate the end effector to grip the tissue.

The technical solution provided according to the embodiments of the present disclosure will be described in detail with reference to the accompanying drawings.

Referring to FIGS. 1 to 11, an end effector 100 for a stapler 10 is shown according to some embodiments of the present disclosure, the end effector 100 includes a knife holder 200 movable between a proximal end and a distal end, and a staple cartridge unit 101 and a staple anvil 102 that are pivotally connected to achieve relative opening and closing. The staple cartridge unit 101 includes a staple cartridge base 103 and a staple cartridge assembly 104 detachably mounted to the staple cartridge base 103.

The knife holder 200 includes a knife holder body 210 and at least one limiting projection 220 disposed near a distal end portion of the knife holder body 210 and extending perpendicularly outward from the knife holder body 210 in a direction away from the knife holder body 210, wherein the limiting projection 200 is arranged between at least one edge 214 of the knife holder body 210 close to the staple cartridge base 103 and a center of the knife holder body 210.

When the staple cartridge assembly 104 is detached or mounted relative to the staple cartridge base 103, the staple cartridge unit 101 is located at an open position, the knife holder 200 is in an initial retraction position, and the limiting projection 220 of the knife holder 200 abuts against a proximal end portion of the staple cartridge base 103 to stop the staple cartridge base 103; and when the knife holder 200 leaves the initial retraction position, the limiting projection 220 of the knife holder 200 is separated from the staple cartridge base 103.

Figure 1:
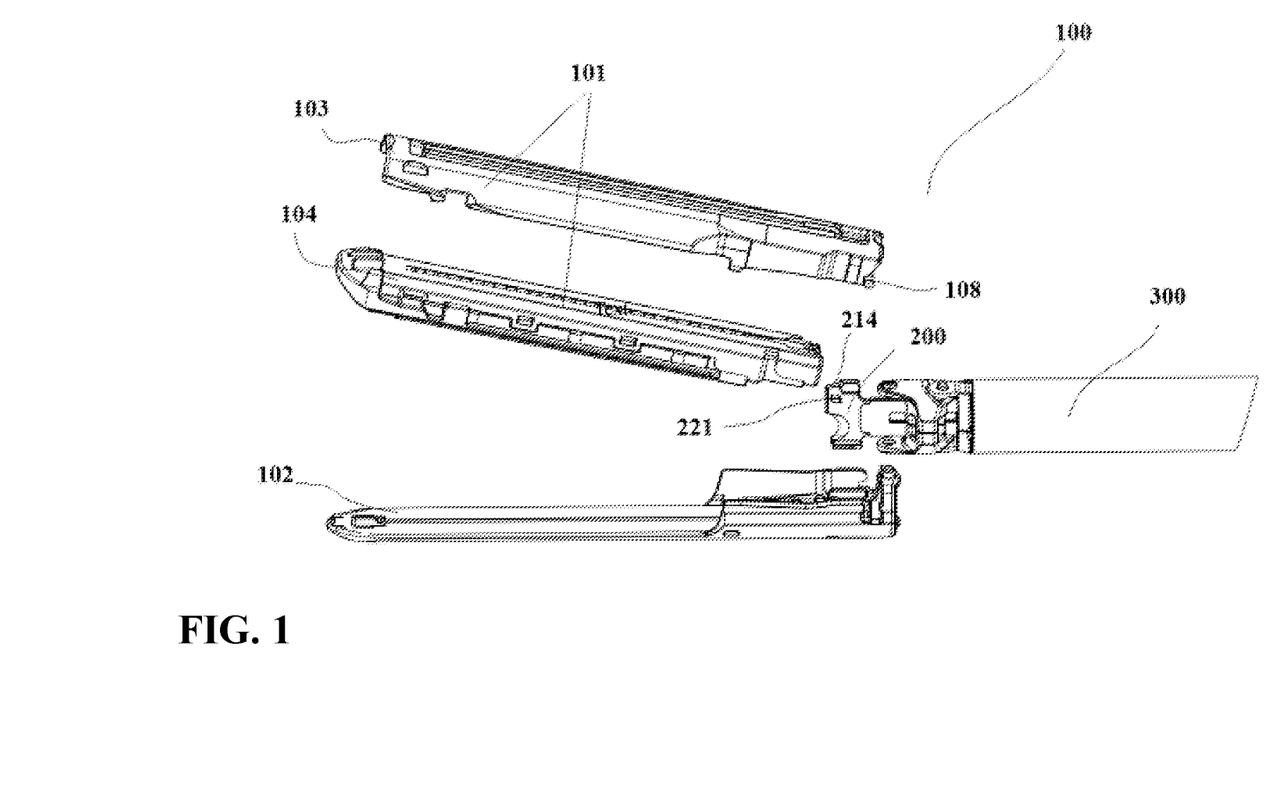
FIG. 1 schematically illustrates an exploded view of an end effector for a stapler according to some embodiments of the present disclosure.
Figure 2:
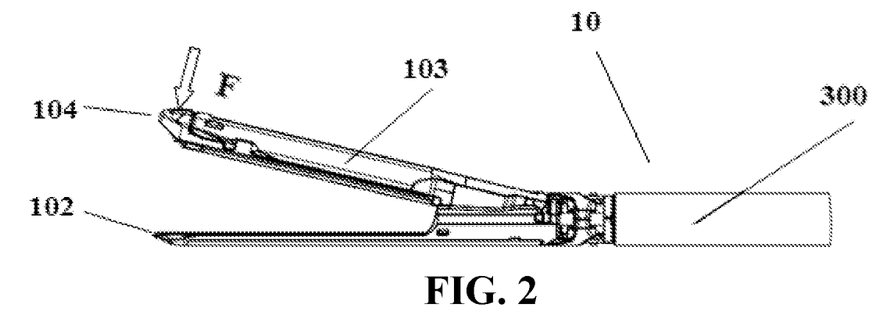
FIG. 2 schematically illustrates an overall view of the end effector for the stapler in FIG. 1 in an open state.
Figure 5:
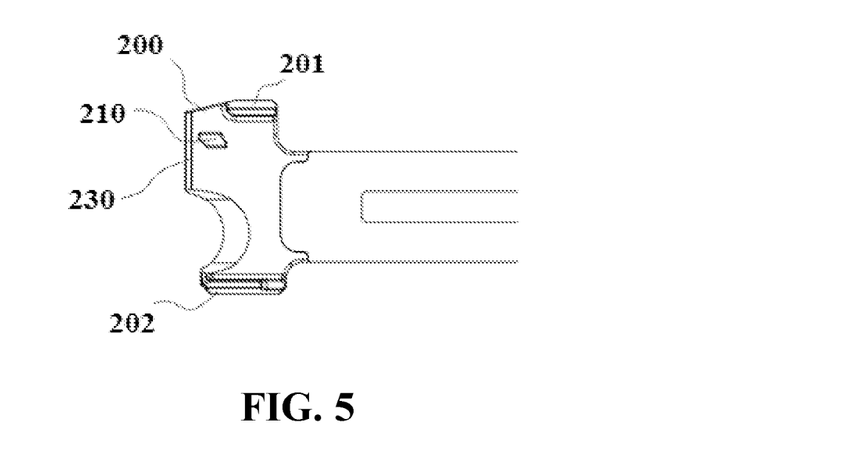
FIG. 5 schematically illustrates a structural diagram of a knife holder of the end effector for the stapler in FIG. 2.

As shown in FIGS. 1 and 2, typically, the staple cartridge assembly 104 may be mounted in a detachable manner to the staple cartridge base 103, and the staple cartridge base 103 may be mounted to the staple anvil 102 via the rotating pivot 108 shown in FIG. 1, so that the staple cartridge unit 101 may pivot relative to the staple anvil 102 in the open position and the closed position. The knife holder 200 may reciprocate in the axial direction by the transmission of the drive rod within the hollow tube 300. Typically, the knife holder 200 may be in the shape of an I-beam, as shown in FIG. 5.

The proximal end portion of the staple cartridge base 103 may be provided with a contact portion 105 corresponding to the limiting projection 220. The limiting projection 220 may have an abutment portion corresponding to the contact portion 105. When the staple cartridge assembly 104 is detached or mounted relative to the staple cartridge base 103, the staple cartridge unit 101 is in the open position relative to the staple anvil 102, the staple cartridge assembly 104 is in the open position relative to the staple cartridge base 103, the knife holder 200 is in the initial retraction position, and the contact portion of the limiting projection 220 of the knife holder 200 can abut against the contact portion 105 of the staple cartridge base 103 to stop the staple cartridge base 105. At this time, by applying an external force F to the staple cartridge assembly 104, as shown in FIG. 2, the staple cartridge assembly 104 and the staple cartridge base 103 can be disassembled/separated. Further, when the knife holder 200 moves toward the distal end in the axial direction away from the initial retraction position, the abutment portion of the limiting projection 220 of the knife holder 200 may be disengaged from the contact portion 105 of the staple cartridge base 103.

Figure 3:
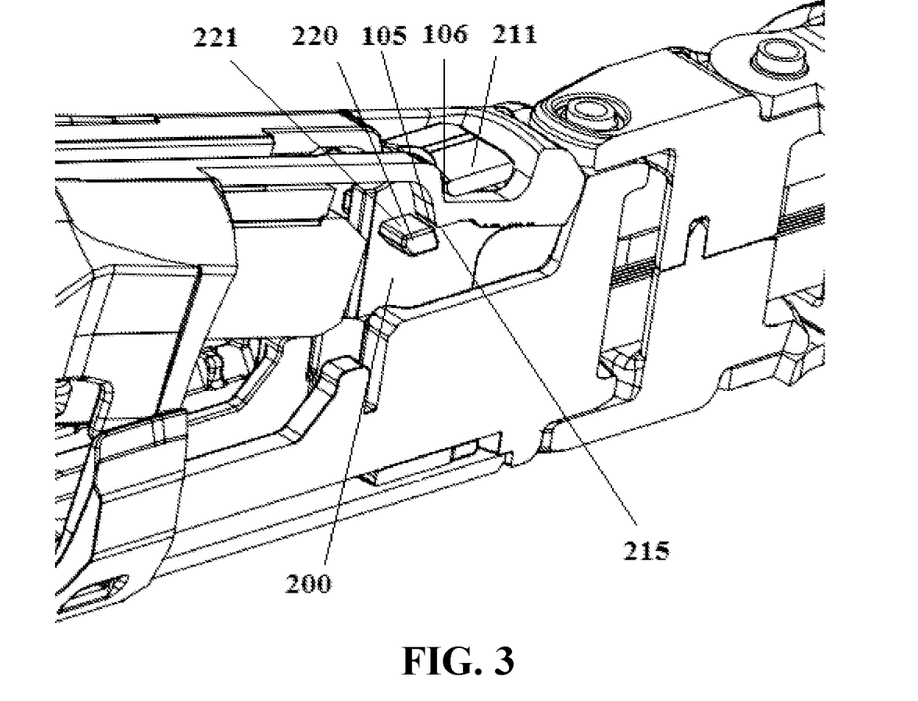
FIG. 3 schematically illustrates a partial perspective view of the end effector for the stapler in FIG. 2.
Figure 13:
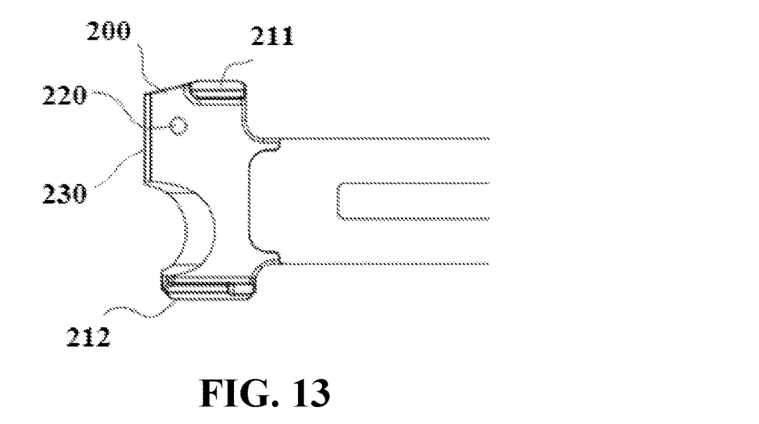
FIG. 13 schematically illustrates a structural diagram of the knife holder of the end effector for the stapler according other some other further embodiments of the present disclosure.
Figure 14:
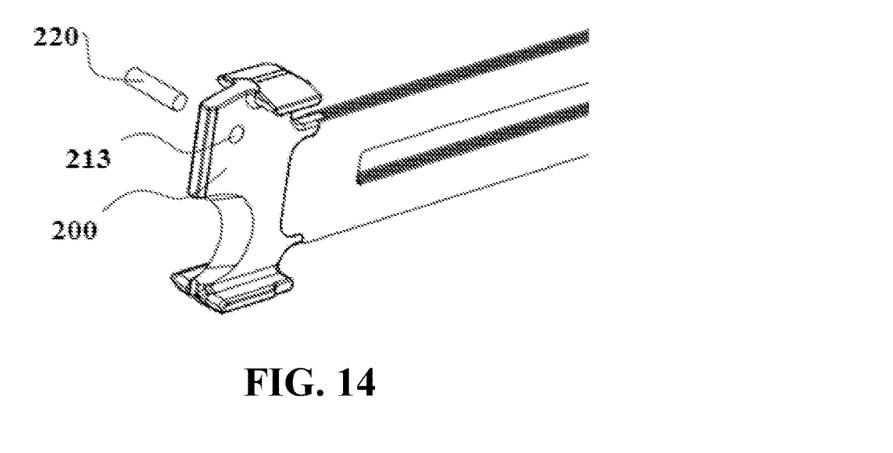
FIG. 14 schematically shows a structural diagram of the knife holder of the end effector for the stapler according to yet some other embodiments of the present disclosure.

Preferably, the abutment portion may be a plane 221 for face-to-face contact with the contact portion 105, as shown in FIGS. 1 and 3, or the abutment portion may also be a linear side edge for line-to-face contact with the contact portion 105, as shown in FIGS. 13 and 14.

In some embodiments, the limiting projection 220 of the knife holder 200 may be formed of a rigid member with a certain rigidity, e.g., it may be made of a metal such as steel, to enable effective stopping of the staple cartridge base 103. Preferably, the limiting projection 220 may be made of the same material as the knife holder body 210. In other embodiments, the limiting projection 220 may be made of a different material from the knife holder body 210.

Figure 4:
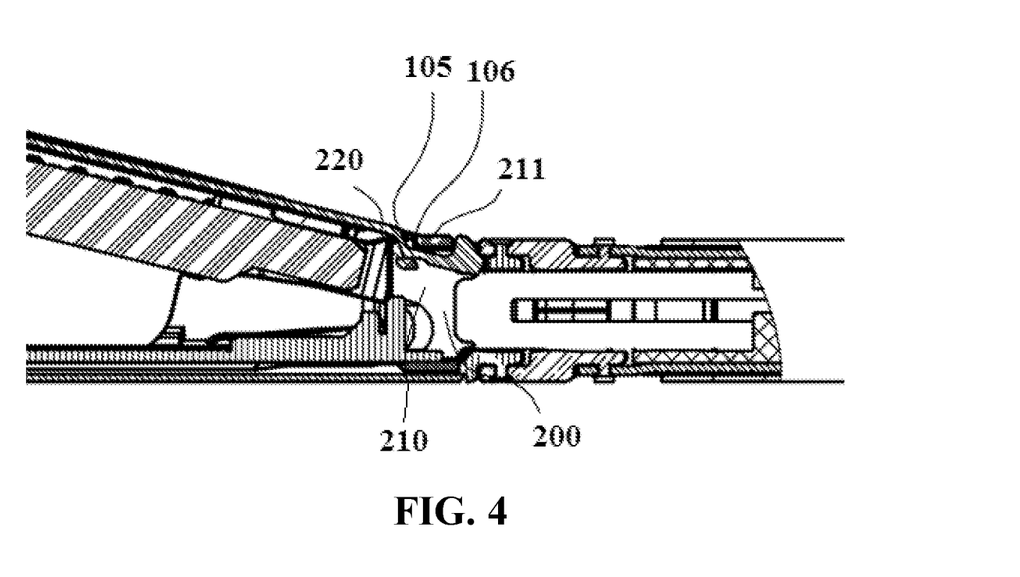
FIG. 4 schematically illustrates a partial sectional view of the end effector for the stapler in FIG. 2.

Further, as shown in FIGS. 1, 3, and 4, in some embodiments, the limiting projection 220 may have a plane 221 facing the above-mentioned at least one edge 214 of the staple cartridge base 103 to achieve stop of the staple cartridge base 103 by face-to-face contact. Specifically, when the limiting projection 220 of the knife holder 200 abuts against the contact portion 105 of the staple cartridge base 103 to stop the staple cartridge base 103, the plane 221 of the limiting projection 220 may contact and abut against the contact portion (contact surface) 105 of the staple cartridge base 103. FIG. 3 schematically shows a state in which the plane 221 of the limiting projection 220 is not in contact with the contact portion (contact surface) 105 of the staple cartridge base 103; and FIG. 4 schematically shows a state in which the plane 221 of the limiting projection 220 and the contact portion (contact surface) 105 of the staple cartridge base 103 are pressed tightly together. At this time, the staple cartridge unit 101 is in the open position, the knife holder 200 is in the initial retraction position, and the staple cartridge assembly 104 is still mounted to the staple cartridge base 103 and in the open position.

Further, in the state of FIG. 4, the contact portion (contact surface) 105 may be parallel to the axial direction of the stapler 10.

Further, in order to increase the friction between the plane 221 and the contact portion (contact surface) 105, the plane 221 may have a certain roughness, for example, the plane 221 may be provided with a texture.

Figure 6:
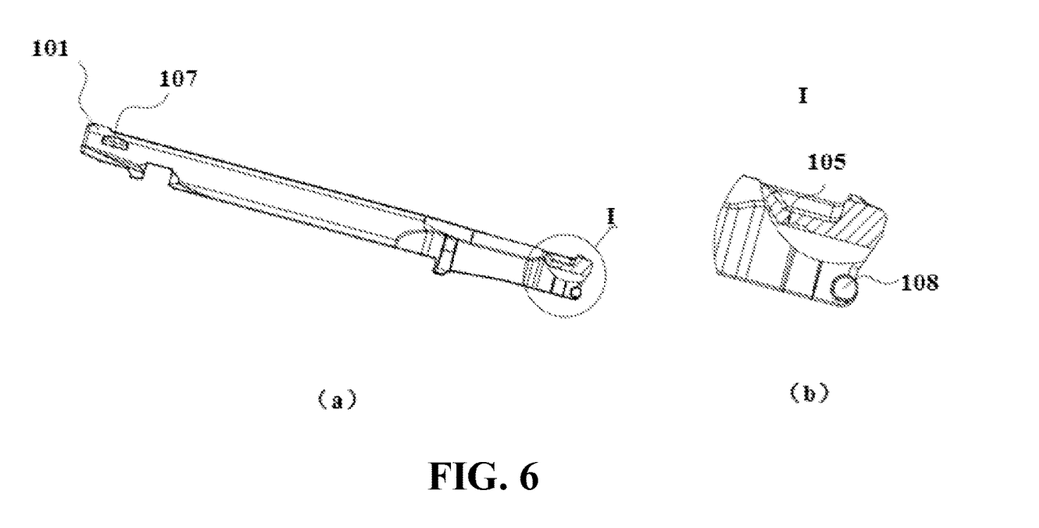
FIG. 6 schematically illustrates a structural diagram of a staple cartridge base of the end effector for the stapler in FIG. 2.
Figure 7:
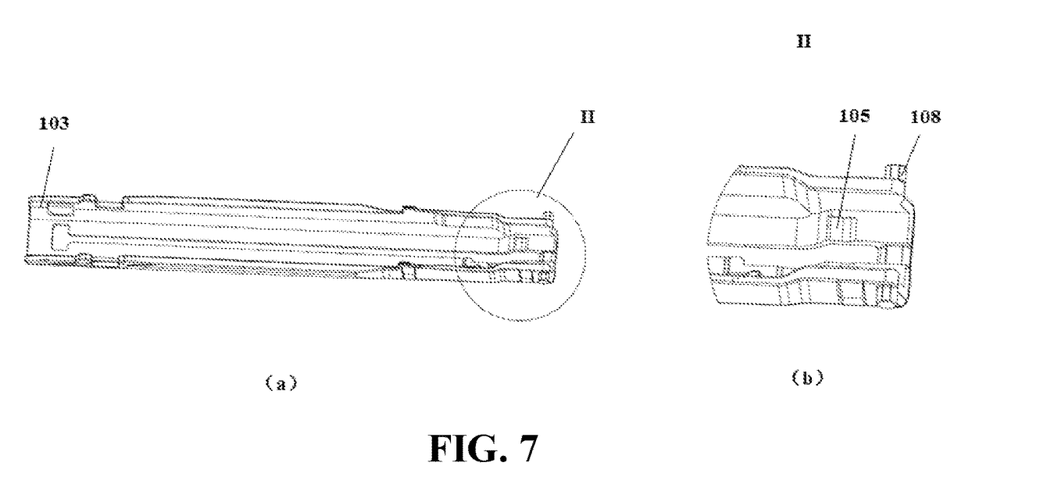
FIG. 7 schematically illustrates a structural diagram of a staple cartridge base of the end effector for the stapler in FIG. 2.

Similarly, the contact portion (contact surface) 105 of the staple cartridge base 103 may have a certain roughness, for example, a texture. Further, in some embodiments, the contact portion (contact surface) 105 of the staple cartridge base 103 may be flat or substantially flat. Typically, in some embodiments, as shown in FIGS. 4 and 5, the contact portion (contact surface) 105 of the staple cartridge base 103 may be flat to increase the contact area with the plane 221 of the limiting projection 220, thereby increasing the friction between the contact portion (contact surface) 105 and the plane 221 such that the limiting projection 220 can effectively resist and stop the staple cartridge base 103. In other alternative embodiments, the contact portion (contact surface) 105 of the staple cartridge base 103 may be substantially flat, for example, as shown in FIGS. 3, 6, and 7, the contact portion 105 may have a recess or be slightly inclined with respect to the plane 221 such that the plane 221 and the contact portion (contact surface) 105 may be easily contacted or disengaged. It is understood that the shape of the contact portion (contact surface) 105 may not be limited to the recess. as long as the shape of the contact portion 105 matches the shape of the corresponding the limiting projection 220. It is suitable as long as the shape of the contact portion 105 matches the shape of the corresponding limiting projection 220.

FIGS. 6 and 7 schematically show the structural diagrams of the staple cartridge base 103 of the end effector 100 for the stapler in FIG. 1 from two perspectives. FIG. 6(a) schematically shows an outside perspective view of the staple cartridge base 103, FIG. 6(b) schematically shows a partial enlarged view at a circle I of the proximal end portion of the staple cartridge base 103 of FIG. 6(a), FIG. 7(a) schematically shows an inside perspective view of the staple cartridge base 103, and FIG. 7(b) schematically shows a partial enlarged view at a circle II of the proximal end portion of the staple cartridge base 103 of FIG. 7(a).

Figure 8:
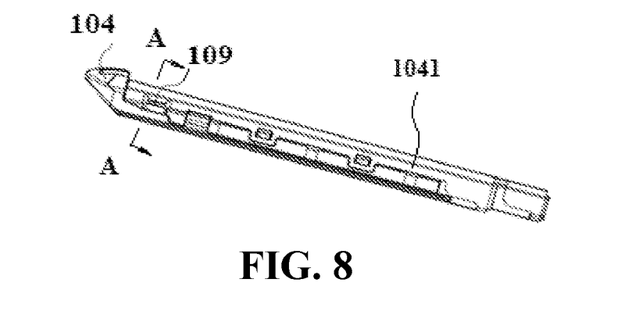
FIG. 8 schematically illustrates an assembled state for the staple cartridge base and the staple cartridge assembly of the end effector for the stapler in FIG. 2.
Figure 9:
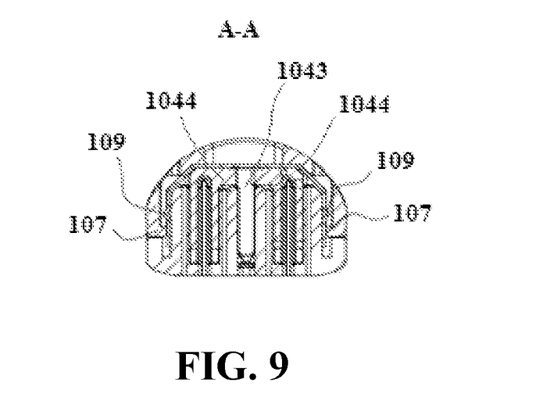
FIG. 9 schematically illustrates a sectional view as viewed along section A-A in FIG. 8.

FIG. 8 schematically illustrates a assembled state where the staple cartridge base 103 and the staple cartridge assembly 104 of the end effector for the stapler in FIG. 2 are assemble, and FIG. 9 schematically shows a sectional view of the staple cartridge unit 101 as viewed along section A-A in FIG. 8. As shown in FIGS. 8 and 9, reference sign 107 may denote a connection structure of the staple cartridge base 103 for connecting the staple cartridge assembly 104, such as a connection hole 107. Reference sign 108 may denote a rotating pivot for mounting the staple cartridge base 103 to the staple anvil 102. Reference sign 109 may denote an elastic projection of the staple cartridge assembly 104 for mating with the staple cartridge base 103.

In some embodiments, the staple cartridge assembly 104 can be disassembled or installed relative to the staple cartridge base 103 by mechanical disassembly or mechanical installation when the limiting projection 220 of the knife holder 220 is against the contact portion 105 of the staple cartridge base 103 to stop the staple cartridge base 103. For example, when the staple cartridge assembly 100 is mounted to the staple cartridge base 103, an external force F may be applied as shown in FIG. 2 so that the abutment portion of the limiting projection 220 abuts against the contact portion 105 of the staple cartridge base 103. Then the elastic projection 109 may be inserted into the connecting hole 107 through an interference fit to connect/assemble the staple cartridge assembly 104 and the staple cartridge base 103 together. And when the staple cartridge assembly 104 is detached from the staple cartridge base 103, the staple cartridge assembly 104 and the staple cartridge base 103 can be detached from each other by applying the external force to the staple cartridge assembly 104 so that the elastic projection 109 is detached from the connecting hole 107 via elastically deformation.

Further, in some embodiments, as shown in FIGS. 1 and 3, the knife holder 200 may include a first wing plate 211 disposed at the edge 214 for closing the staple cartridge unit 101, and a space 215 between the limiting projection 220 and the first wing plate 211. As shown in FIGS. 3 and 4, the proximal end portion of the staple cartridge base 103 may slide back and forth in the space 215 when the staple cartridge unit 101 pivots relative to the staple anvil 102 between the open and closed positions.

Figure 10:
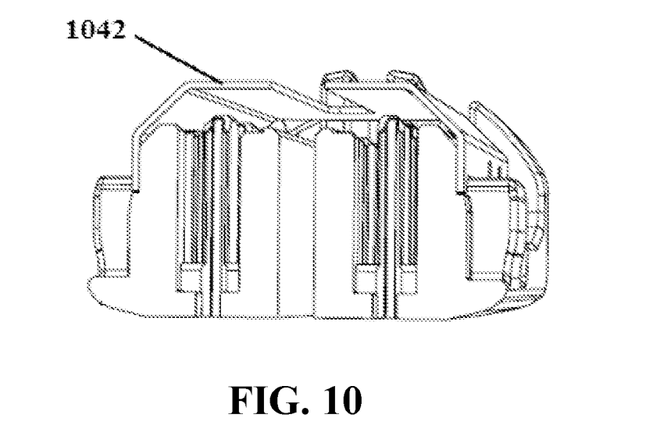
FIG. 10 schematically illustrates a structural diagram of a guide channel in the staple cartridge assembly in FIG. 9.
Figure 11:
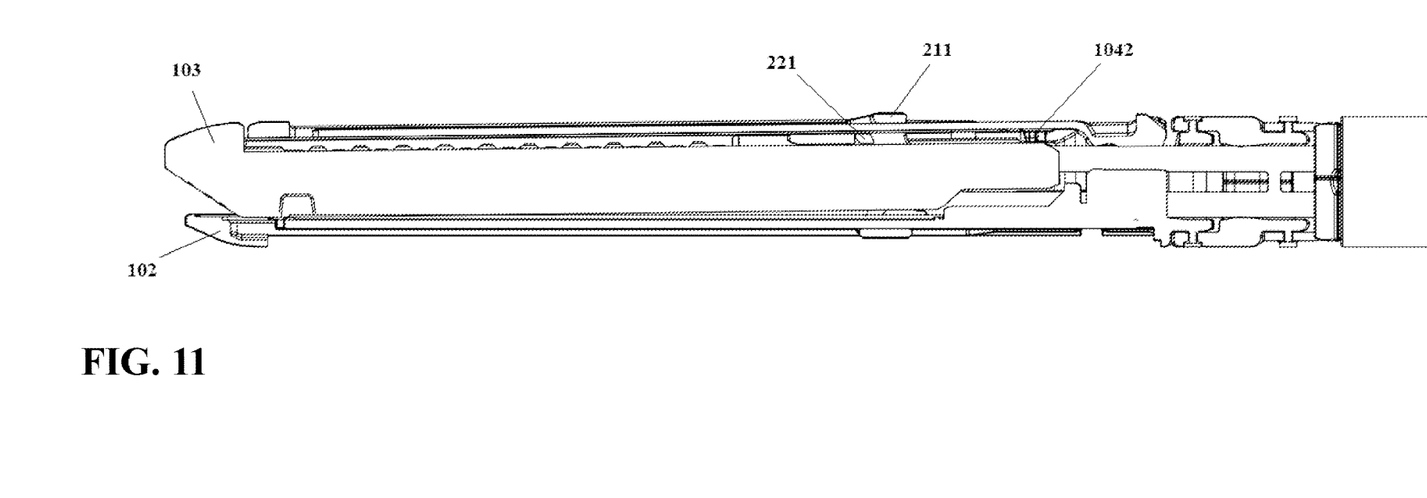
FIG. 11 schematically illustrates a structural diagram of the end effector for the stapler in FIG. 2 in a closed state.

Further, referring to FIGS. 9 to 11, the staple cartridge 104 may include a U-shaped staple cartridge 1041 and a cover plate 1042 disposed inside the staple cartridge 1041 and extending in the U-shaped circumferential direction of the staple cartridge 1041 such that a cross-shaped guide channel 1043 may be provided between the staple cartridge 1041 and the cover plate 1042. As the knife holder 200 moves toward the distal end in an axial direction away from the initial retraction position to drive the staple cartridge unit 101 to pivot to the closed position, the limiting projection 220 may be disengaged from the proximal end portion of the staple cartridge base 103 so that the knife holder 200 may move through within the guide channel 1043. In a preferred embodiment, as shown in FIGS. 9 and 10, the cross-shape of the guide channel 1043 may be configured to include an intermediate body portion for allowing the knife holder body 210 to move through, and a lateral gap 1044 perpendicular to the intermediate body portion and extending to two sides in a direction away from the intermediate body portion for allowing the limiting projection 220 to move through. The intermediate body portion may be shape-matched with the knife holder body 210 such that the knife holder body 210 may freely slide within the intermediate body portion. Also, the lateral gap 1044 may be shape-matched with the limiting projection 220 such that the limiting projection 220 may freely slide within the lateral gap 1044.

Further, the knife holder body 210 may have a distal end portion 230. As shown in FIG. 5, the staple cartridge assembly 104 may further include a staple driver for pushing out a titanium staple, and a movable slider arranged in the intermediate body portion. The slider may be initially arranged at a proximal end of the intermediate body portion, as the knife holder 200 moves toward a distal end in an axial direction. The knife holder body 210 may move into the intermediate body portion. And at the same time, the limiting projection 220 moves into the lateral gap 1044, and with the knife holder 200 moving, the distal end portion 230 of the knife holder body 210 may push the slider to slide in the intermediate body portion, so that the slider is capable of pushing the staple driver in the intermediate body portion to push out the titanium staple.

Specifically, in a state where the staple cartridge assembly 104 is mounted to the staple cartridge base 103, as the knife holder 200 moves toward the distal end in the axial direction away from the initial retraction position, on the one hand, the first wing plate 211 on the knife holder 200 can abut against the side surface of the proximal end of the staple cartridge base 103 to press the staple cartridge base 103, so that the contact portion 105 of the staple cartridge base 103 moves away from the contact portion of the limiting projection 220. And then, because the staple cartridge base 103 is continuously subjected to the pressure exerted by the first wing plate 211, the staple cartridge unit 101 can rotate relative to the staple anvil 102 to close. Meanwhile, on the other hand, during closing of the staple cartridge unit 101 with respect to the staple anvil 102, the knife holder 200 continues to move toward the U-shaped staple cartridge 1041 within the staple cartridge assembly 104 into the guide channel 1043 between the staple cartridge 1041 and the cover plate 1042, where the knife holder body 210 can slide within the intermediate body portion while the limiting projection 220 can slide within the lateral gap 1044.

Further, the slider may be disposed at the proximal end of the guide channel 1043 and more specifically within the intermediate body portion at the beginning of the closing process. As the knife holder 200 moves toward the distal end in the axial direction away from the initial retraction position to the proximal end of the guide channel 1043, the distal end portion 230 of the knife holder body 210 may begin to move into the intermediate body portion of the guide channel 1043 and come into contact with the slider at the initial position. As the knife holder 200 continues to move toward the distal end, the distal end portion 230 of the knife holder body 210 can push the slider to slide within the intermediate body portion of the guide channel 1043, so that the slider can push the staple driver to thereby push out the titanium staple for anastomosis operation. Meanwhile, the limiting projection 220 can slide within the lateral gap 1044. And after the anastomosis/firing is completed, the slider can be pushed to the distal end within the pilot channel 1043 and retained at the distal end. At this time, the knife holder 200 can be retracted to the initial retraction position, and then a new staple cartridge assembly 104 can be replaced. For the specific content of the knife holder 200 pushing staple driver to push out the titanium staple, please refer to the prior art.

With reference to FIGS. 1 to 11, a process of disassembly and installation of the staple cartridge assembly 104 with respect to the staple cartridge base 103 will be described below.

First, the disassembly process of the staple cartridge assembly 104 relative to the staple cartridge base 103 is described.

When the staple cartridge assembly 104 is disassembled relative to the staple cartridge base 103, first referring to FIG. 2, the knife holder 200 is moved back to the initial retraction position and the staple cartridge unit 101 is opened to the open position. Next, referring to FIGS. 2 and 3, an external force F is exerted to the staple cartridge base 103 as indicated by the arrow in FIG. 2. The staple cartridge base 103 can be rotated toward the knife holder 200 such that the abutment portion of the limiting projection 220 of the knife holder 200 contacts and abuts against the contact portion 105 of the staple cartridge base 103 to stop the staple cartridge base 103. By way of example, the plane 221 of the limiting projection 220 can contact and abuts against the contact portion 105 of the staple cartridge base 103, as shown in FIG. 4. Next, in a state where the staple cartridge base 103 is not moved, the external force may be continued to be applied to mechanically detach the staple cartridge assembly 104 from the staple cartridge base 103. For example, as shown in FIGS. 8 and 9, an external force may be applied so that the elastic projection 109 of the staple cartridge assembly 104 may elastically deform to disengage from the connecting hole 107 of the staple cartridge base 103, thereby disengaging the staple cartridge assembly 104 and the staple cartridge base 103 from each other.

Next, the installation process of the staple cartridge assembly 104 relative to the staple cartridge base 103 is described.

First, the knife holder 200 is moved back to the initial retraction position and the staple cartridge unit 101 is opened to the open position. Next, referring to FIG. 3, an external force F is exerted to the staple cartridge base 103, the staple cartridge base 103 can be rotated toward the knife holder 200 such that the abutment portion of the limiting projection 220 of the knife holder 200 contacts and abuts against the contact portion 105 of the staple cartridge base 103 to stop the staple cartridge base 103. By way of example, the plane 221 of the limiting projection 220 can contact and abuts against the contact portion 105 of the staple cartridge base 103. Next, in a state where the staple cartridge base 103 is not moved, the external force may continue to be applied to mechanically mount the staple cartridge assembly 104 to the staple cartridge base 103, for example, the external force may be applied such that the elastic projection 109 of the staple cartridge assembly 104 may elastically deform to be inserted into the connection hole 107 of the staple cartridge base 103, so that the staple cartridge assembly 104 and the staple cartridge base 103 may be connected and assembled together with each other.

When operating with the stapler 10, the knife holder 200 can be extended by actuating the drive rod to move it away from the initial retraction position, thereby driving the limiting projection 220 away from the contact portion (contact surface) 105 of the staple cartridge base 103. While the knife holder 200 is extended, the first wing plate 201 of the knife holder 200 exerts a closing force on the staple cartridge base 103, and the staple cartridge base 103 can rotate along the guide surface 106 shown in FIG. 6, thus driving the staple cartridge unit 101 to close relative to the staple anvil 102, so that the staple cartridge unit 101 and the staple anvil 102 can grip human tissue for surgical operation. In the above closing process, the knife holder 200 is slidable within the guide channel 1043 between the staple cartridge 1041 and the cover plate 1042, where the knife holder body 210 is slidable within the intermediate body portion and the limiting projection 220 is slidable within the lateral gap 1044 such that the knife holder body 230 of the distal end portion 210 can push the slider to slide within the intermediate body portion such that the slider pushes the staple driver to push out the titanium staple.

As can be seen from the above, by virtue of the fixing effect of the limiting projection 220 on the staple cartridge base 103, the staple cartridge assembly 104 can be easily disassembled and installed with respect to the staple cartridge base 103, so that the staple cartridge unit 101 can be disassembled, installed and replaced conveniently and quickly.

Furthermore, by providing the contact portion 105 of the staple cartridge base 103 and the abutment portion of the limiting projection 220 cooperating with the contact portion 105, the friction force between the limiting projection 220 and the staple cartridge base 103 can be increased, so that the staple cartridge base 103 can be more firmly pressed against the limiting projection 220.

Further, by providing the guide channel 1043 for the knife holder 200 to move through at the staple cartridge assembly 104, the knife holder 220 can move stably within the staple cartridge assembly 104 without interfering with the operation of other parts of the staple cartridge assembly 104. Further, a movable slider may also be provided within the intermediate body portion of the guide channel 1043 of the staple cartridge assembly 104, so that as the knife holder 200 moves within the staple cartridge assembly 104, the distal end portion 230 of the knife holder body 210 pushes the slider to slide within the intermediate body portion, so that the slider can conveniently push the staple driver within the staple cartridge assembly 104 to push out the titanium staple.

Further, at least one limiting projection 220 may be provided on each side of the knife holder body 210.

Further, the limiting projection 220 can be integrally formed with the knife holder body 210. Alternatively, the limiting projection 220 may be formed separately with respect to the knife holder body 210 in which case the limiting projection 220 may be fixedly connected to the knife holder body 210.

Referring to FIGS. 5 and 12-14, in some embodiments, the longitudinal section of the limiting projection 220 may be in a polygonal or circular shape.

Further, referring to FIG. 7, in some embodiments, the limiting projection 220 may be a column having a convex hexagonal longitudinal section. Thus, in such an example, there is a face-to-face contact between the limiting projection 220 and the staple cartridge base 103 or the contact portion 105.

Figure 12:
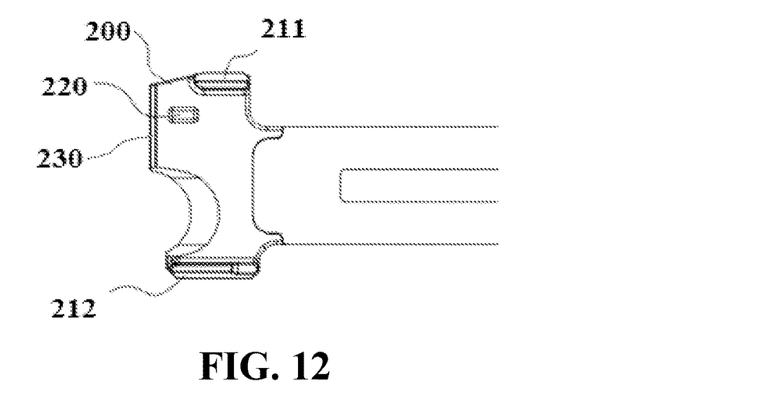
FIG. 12 schematically illustrates a structural diagram of the knife holder of the end effector for the stapler according to some further embodiments of the present disclosure.

Further, referring to FIG. 12, in still other embodiments, the limiting projection 220 may be a square cylinder. Thus, in such an example, there is a face-to-face contact between the limiting projection 220 and the staple cartridge base 103 or the contact portion 105. Reference sign 212 may denote a second wing 212 of the limiting projection 220 opposite the first wing plate 211.

In the above-described embodiment, the axial plane 221 of the convex hexagonal cylinder and the square cylinder having regular shapes is flat, so that when the limiting projection 220 comes into face-to-face contact with the staple cartridge base 103 or the contact portion 105 with a larger contact area and greater the friction force, and is subject to more uniform force.

Further, referring to FIG. 13, in other embodiments, the limiting projection 220 may be a cylinder. In this example, the limiting projection 220 is in line-surface contact with the staple cartridge base 103 or the contact portion 105, but the cylindrical shape makes the limiting projection 220 easy to manufacture and easy to install. Reference sign 212 may denote a second wing 212 of the limiting projection 220 opposite the first wing plate 211.

Further, in yet other embodiments, the limiting projection 220 may be secured to the knife holder 200. Preferably, the limiting projection 220 may be welded to the surface of the knife holder 200 as shown in FIG. 7.

Further, in other embodiments, the limiting projection 220 may also be removably mounted to a surface of the knife holder 200 such as by plugging in, etc. In this example, the limiting projection 220 is exchangeable, thereby increasing the service life of the knife holder 200.

Further, referring to FIG. 14, in some embodiments, the knife holder 200 may be provided with a through hole 213 penetrating through the knife holder body 210 between the edge 214 and the center of the knife holder body 210, and the limiting projection 220 may be a pin inserted in an interference fit to the through hole 203 of the knife holder body 210, and the pin extends from the through hole 203 by a proper length. The pin may extend from the through hole 203 to such a length that, when the staple cartridge base 103 is rotationally approaching the limiting projection 220, the pin effectively abuts the contact portion 105 at the proximal end portion of the staple cartridge base 103 and stops the staple cartridge base 103 without interfering with the normal operation of the rest of the end effector 100.

Further, the end effector 100 for the stapler according to any one of the above-described embodiments is applicable for an endoscopic cutting stapler.

The present disclosure may be particularly applicable to but not limited to the endoscopic cutting stapler and may also be applicable to other suitable stapler as the case may be.

The operation mode of the end effector 100 for the stapler according to some embodiments of the present disclosure is described below by way of example with reference to the endoscopic cutting stapler. In this example, the staple cartridge assembly 104 may be disposable, and the limiting projection 220 may be of a hexagonal boss configuration.

First, the disassembly process of the staple cartridge assembly 104 relative to the staple cartridge base 103 is described.

Referring to FIGS. 1-4, during an operation of the endoscopic cutting stapler, the staple anvil 102 may be fixed and the disposable staple cartridge assembly 104 may be rotated about the hollow tube 300 to close or open the jaws of the end effector 100 for clamping or releasing tissue. When the jaw is closed, the I-beam knife holder 200 can be driven forward by the drive rod of the stapler 10 to close the jaw. When the jaw is opened, the I-beam knife holder 200 can be driven back by the drive rod of the stapler 10, and then the elastic clip on the staple anvil 102 bounces the staple cartridge assembly 104 to open the jaw.

As shown in FIG. 4, the limiting projection 220 may be disposed on the lower left side of the first wing plate 211. The proximal end portion of the staple cartridge base 103 may pass through the space 215 between the limiting projection 220 and the first wing plate 2111. As shown in FIGS. 3 and 4, the proximal end portion of the staple cartridge base 103 may have a recessed contact portion 105 facing the limiting projection 220 and a guide surface 106 facing the first wing plate 211.

When the disposable staple cartridge assembly 104 is removed and replaced after the surgical operation is completed, the knife holder 200 can be pulled to the initial retraction position, while the staple cartridge unit 101 is in the open position. Then, as indicated by the arrow in FIG. 2, the external force F for dissembling can be applied, and the staple cartridge base 103 is rotated toward the limiting projection 220, so that the contact portion 105 of the staple cartridge base 103 contacts and abuts against the limiting projection 220, whereby the staple cartridge base 103 is stopped and fixed, while the staple cartridge assembly 100 mounted to the staple cartridge base 103 does not rotate about the hollow tube 300. When a mechanical external force is further applied, the structure of the elastic projection 109 can be elastically deformed so that the staple cartridge assembly 104 and the staple cartridge base 103 can be detached from each other and the staple cartridge assembly 100 can be easily and quickly removed.

Next, the installation process of the staple cartridge assembly 104 relative to the staple cartridge base 103 is described.

The knife holder 200 is moved back to the initial retraction position and the staple cartridge unit 101 is opened to the open position. Next, referring to FIG. 3, the external force is applied to the staple cartridge base 103, and the staple cartridge base 103 may rotate toward the knife holder 200 such that the axial plane 221 of the limiting projection 220 contacts and abuts against the contact portion 105 of the staple cartridge base 103. Next, in a state where the staple cartridge base 103 is not moved, an external force may be continuously applied such that the elastic projection 109 of the staple cartridge assembly 104 may elastically deform to be inserted into the connection hole 107 of the staple cartridge base 103, so that the staple cartridge assembly 104 and the staple cartridge base 103 may be connected and assembled together with each other.

When operating with the stapler 10, the knife holder 200 can be extended by actuating the drive rod to move it away from the initial retraction position, thereby driving the limiting projection 220 away from the contact portion 105 of the staple cartridge base 103. While the knife holder 200 is extended, the first wing plate 201 of the knife holder 200 exerts a closing force on the staple cartridge base 103, and the staple cartridge base 103 can rotate along the guide surface 106 shown in FIG. 6, thus driving the staple cartridge unit 101 to close relative to the staple anvil 102, so that the staple cartridge unit 101 and the staple anvil 102 can grip human tissue for surgical operation. In the above closing process, the knife holder 200 is slidable within the guide channel 1043 between the staple cartridge 1041 and the cover plate 1042, where the knife holder body 210 is slidable within the intermediate body portion and the limiting projection 220 is slidable within the lateral gap 1044 such that the knife holder body 230 of the distal end portion 210 can push the slider to slide within the intermediate body portion such that the slider pushes the staple driver to push out the titanium staple.

To sum up, the present disclosure enables the staple cartridge assembly of the end effector to be conveniently removed from and mounted to the staple cartridge base, thereby making the installation, removal and replacement of the staple cartridge unit easy and quick.

It should be noted that the terms "include", "comprise" or any other variation thereof are intended to cover non-exclusive inclusion, so that a process, method, article, or apparatus that includes a set of elements includes not only those elements, but also other elements not expressly listed, or also include elements that are inherent to such process, method, article, or apparatus. Without further limitation, the elements defined by the statement "comprising a . . . " do not preclude the existence of additional identical elements in the process, method, article, or apparatus that include said elements.

Finally, it should be noted that, the above embodiments are only used to illustrate the technical solution of the present disclosure and not to limit it. Although the present disclosure has been described in detail with reference to the foregoing embodiments, it should be understood by those of ordinary skill in the art that the technical solution described in the foregoing embodiments can still be modified or some of the technical features thereof can be equivalently replaced. However, these modifications or substitutions do not depart the essence of the corresponding technical solution from the spirit and scope of the technical solution of each embodiment of the present disclosure.

List of Reference Signs

10: stapler
100: end effector
101: staple cartridge unit
102: staple anvil
103: staple cartridge base
104: staple cartridge assembly
1041: staple cartridge
1042: cover plate
1043: guide channel
1044: lateral gap
105: contact portion
106: guide surface
107: connection structure
108: rotating pivot
109: elastic projection
200: knife holder
210: knife holder body
211: first wing plate
212: second wing plate
213: through hole
214: edge
215: space
220: limiting projection
221: axial plane
230: distal end portion
300: hollow tube
F: external force

What is claimed is:

1. An end effector for a stapler, comprising: a knife holder moving in an axial direction, and a staple cartridge unit and a staple anvil, pivotally connected to achieve relative opening and closing, wherein the staple cartridge unit comprises a staple cartridge base and a staple cartridge assembly detachably mounted to the staple cartridge base;

wherein the knife holder comprises a knife holder body and at least one limiting projection disposed near a distal end portion of the knife holder body and extending perpendicularly outward from the knife holder body in a direction away from the knife holder body, wherein the limiting projection is arranged between at least one edge of the knife holder body close to the staple cartridge base and a center of the knife holder body; and when the staple cartridge assembly is detached from or mounted to the staple cartridge base, the staple cartridge unit is in an open position, the knife holder is in an initial retraction position, and the limiting projection of the knife holder abuts against a proximal end portion of the staple cartridge base to stop the staple cartridge base, and when the knife holder leaves the initial retraction position, the limiting projection of the knife holder is separated from the staple cartridge base.

2. The end effector according to claim 1, wherein the proximal end portion of the staple cartridge base is provided with a contact portion corresponding to the limiting projection, the limiting projection is provided with an abutment portion corresponding to the contact portion, and when the limiting projection of knife holder abuts against the contact portion of the staple cartridge base to stop the staple cartridge base, the abutment portion of limiting projection contacts and abuts against the contact portion of the staple cartridge base.

3. The end effector according to claim 2, wherein the abutment portion is a plane for face-to-face contact with the contact portion or a linear side edge for line-to-face contact with the contact portion.

4. The end effector according to claim 2, wherein a contact surface of the staple cartridge base is flat or substantially flat.

5. The end effector according to claim 1, wherein the limiting projection of the knife holder is made of metal or steel.

6. The end effector according to claim 1, wherein the knife holder comprises a first wing plate disposed at the at least one edge for closing the staple cartridge unit and a space between the limiting projection and the first wing plate, when the staple cartridge unit pivots relative to the staple anvil between an open position and a closed position, the proximal end portion of the staple cartridge base reciprocates within the space.

7. The end effector according to claim 1, wherein the limiting projection is integrally formed with the knife holder body; or the limiting projection is fixedly connected to the knife holder body.

8. The end effector according to claim 7, wherein a longitudinal section parallel to an axial direction of the limiting projection is in a polygonal or circular shape.

9. The end effector according to claim 8, wherein the limiting projection is a column having a convex hexagonal longitudinal section, or a square column, or a cylinder.

10. The end effector according to claim 1, wherein the limiting projection is welded to the knife holder body.

11. The end effector according to claim 1, wherein the knife holder is provided with a through hole penetrating through the knife holder body between the at least one edge and the center of the knife holder body.

12. The end effector according to claim 11, wherein the limiting projection is a pin inserted in an interference fit to the through hole of the knife holder, and the pin extending from the through hole by a proper length.

13. The end effector according to claim 1, wherein the staple cartridge assembly comprises a U-shaped staple cartridge and a cover plate arranged inside the staple cartridge and extending along a U-shaped circumferential direction of the staple cartridge, so that a cross-shaped guide channel is arranged between the staple cartridge and the cover plate, when the knife holder leaves the initial retraction position and moves toward a distal end in an axial direction to drive the staple cartridge unit to pivot to the closed position, the limiting projection is disengaged from the proximal end portion of the staple cartridge base to move the knife holder through the guide channel.

14. The end effector according to claim 13, wherein the cross-shape of the guide channel is configured to comprise an intermediate body portion for allowing the knife holder body to move through, and a lateral gap perpendicular to the intermediate body portion and extending to two sides in a direction away from the intermediate body portion for allowing the limiting projection to move through.

15. The end effector according to claim 14, wherein the staple cartridge assembly further comprises a staple driver for pushing out a titanium staple, and a movable slider arranged in the intermediate body portion, the slider being initially arranged at a proximal end of the intermediate body portion, and when the knife holder moves toward a distal end in the axial direction, the knife holder body moves into the intermediate body portion, and at the same time the limiting projection moves into the lateral gap, and with the knife holder moving, the distal end portion of the knife holder body pushes the slider to slide in the intermediate body portion, so that the slider is capable of pushing the staple driver in the intermediate body portion to push out the titanium staple.

16. The end effector according to claim 1, wherein the end effector is applicable for an endoscopic cutting stapler.

* * * * *